United States Patent [19]

Samuels et al.

[11] Patent Number: 5,582,168

[45] Date of Patent: *Dec. 10, 1996

[54] APPARATUS AND METHODS FOR MEASURING CHARACTERISTICS OF BIOLOGICAL TISSUES AND SIMILAR MATERIALS

[75] Inventors: Mark A. Samuels, Duluth; Scott W. Patterson, Lawrenceville; Jonathan A. Eppstein, Atlanta, all of Ga.; Nai T. Yu, Kowloon, Hong Kong; Sven–Erik Bursell, Newton, Mass.

[73] Assignee: Georgia Tech Research Corp., Atlanta, Ga.

[ * ] Notice: The portion of the term of this patent subsequent to Apr. 20, 2010, has been disclaimed.

[21] Appl. No.: 7,584

[22] Filed: Jan. 22, 1993

Related U.S. Application Data

[63] Continuation-in-part of Ser. No. 731,533, Jul. 17, 1991, Pat. No. 5,203,328.

[51] Int. Cl.$^6$ ........................................................ A61B 5/00
[52] U.S. Cl. ........................................ 128/633; 351/221
[58] Field of Search .............................. 128/633–4, 664–5; 356/39–41; 351/221

[56] References Cited

U.S. PATENT DOCUMENTS

| | | |
|---|---|---|
| 3,948,248 | 4/1976 | Zuckerman et al. . |
| 3,958,560 | 5/1976 | March . |
| 4,014,321 | 3/1977 | March . |
| 4,350,163 | 9/1982 | Ford, Jr. et al. . |
| 4,412,543 | 11/1983 | Vassiliadis et al. . |
| 4,548,498 | 10/1985 | Folestad et al. . |
| 4,573,778 | 3/1986 | Shapiro . |
| 4,582,405 | 4/1986 | Müller et al. . |
| 4,589,354 | 2/1986 | Shapiro et al. . |

(List continued on next page.)

FOREIGN PATENT DOCUMENTS

| | | |
|---|---|---|
| 261957 | 11/1988 | Germany . |
| 261957A1 | 11/1988 | Germany . |
| WO93/07801 | 4/1993 | WIPO . |

OTHER PUBLICATIONS

"Laser instrument gets jump on cataracts," *Machine Design* Sep. 7, 1989, pp. 14–15.

Abstract of "Optical Fiber Type Temperature Distribution Measuring Apparatus," Patent Abstracts of Japan, Jun. 29, 1989, vol. 13, No. 284.

G. Bessems, et al., "Non–Tryptophan Fluorescence of Crystallins From Normal and Cataractous Human Lenses," *Investigative Ophthalmology & Visual Science*, Jul. 1987, vol. 28, pp. 1157–1163.

J. Bleeker, et al., "Autofluorescence of the Lens in Diabetic and Healthy Subjects by Fluorophotometry," *Investigative Ophthalmology & Visual Science*, May 1986, vol. 27, No. 5, pp. 791–794.

J. Helve, et al., "Autofluorescence of the Human Diabetic lens in Vivo," *American Journal of Ophthalmology*, Apr. 1976, vol. 81, No. 4, pp. 491–494.

Hockwin, et al., "Investigations on Lens Transparency and its Disturbances by Microdensitometric analysis of Scheimpflug Photographs," *Current Eye Research*, 1984, vol. 3, No. 1, pp. 15–22.

R. Jacobs, et al., "Fluorescence Intensity Profile of Human Lens Sections," *Investigative Ophthalmology & Visual Science*, Jan. 1981, vol. 20, No. 1, pp. 117–120.

R. Lendrum, et al., "Islet–Cell Antibodies in Diabetes Mellitus," *The Lancet*, Dec. 11, 1976, pp. 1273–1275.

(List continued on next page.)

*Primary Examiner*—Angela D. Sykes
*Attorney, Agent, or Firm*—Dean W. Russell; Kilpatrick & Cody

[57] ABSTRACT

Apparatus and methods for characterizing biological tissues and other turbid media with normalization that serves to compensate for the effects of scattering, reflectance, and absorption are disclosed.

19 Claims, 6 Drawing Sheets

U.S. PATENT DOCUMENTS

| | | |
|---|---|---|
| 4,592,361 | 6/1986 | Parker et al. . |
| 4,675,300 | 6/1987 | Zare et al. . |
| 4,702,576 | 10/1987 | Magnante ............................ 128/633 X |
| 4,711,540 | 12/1987 | Yoshino et al. . |
| 4,711,541 | 12/1987 | Yoshino et al. . |
| 4,711,542 | 12/1987 | Ichihashi et al. . |
| 4,758,081 | 7/1988 | Barnes . |
| 4,776,687 | 10/1988 | Nakanishi et al. . |
| 4,781,453 | 11/1988 | Kobayashi . |
| 4,832,043 | 5/1989 | Ichihashi . |
| 4,832,483 | 5/1989 | Verma . |
| 4,836,207 | 6/1989 | Bursell et al. ...................... 128/665 X |
| 4,838,683 | 6/1989 | Ichihashi et al. . |
| 4,842,401 | 6/1989 | Maurice . |
| 4,848,897 | 7/1989 | Aizu et al. . |
| 4,852,987 | 8/1989 | Lohmann . |
| 4,854,693 | 8/1989 | Ichihashi et al. . |
| 4,863,261 | 9/1989 | Flammer . |
| 4,877,322 | 10/1989 | Hill .................................... 128/633 X |
| 4,882,492 | 11/1989 | Schlager . |
| 4,883,351 | 11/1989 | Weiss . |
| 4,895,159 | 1/1990 | Weiss . |
| 4,900,145 | 2/1990 | Akiyama . |
| 4,941,741 | 7/1990 | Mizuta . |
| 4,950,068 | 8/1990 | Mizuta . |
| 4,957,113 | 9/1990 | Benedek ................................. 128/665 |
| 4,988,184 | 1/1991 | Akiyama . |
| 4,991,954 | 2/1991 | Akiyama . |
| 4,993,827 | 2/1991 | Benedek et al. . |
| 5,000,562 | 3/1991 | Ichihashi et al. . |
| 5,025,785 | 6/1991 | Weiss ..................................... 128/633 |
| 5,042,494 | 8/1991 | Alfano ................................... 128/665 |
| 5,072,731 | 12/1991 | Taratuta et al. ......................... 128/633 |
| 5,120,123 | 6/1992 | Akiyama . |
| 5,137,355 | 8/1992 | Barbour et al. . |
| 5,139,022 | 8/1992 | Lempert . |
| 5,158,090 | 10/1992 | Waldman et al. ...................... 128/664 |
| 5,186,173 | 2/1993 | Zuckerman . |
| 5,203,328 | 4/1993 | Samuels et al. ........................ 128/633 |
| 5,204,705 | 4/1993 | Akiyama et al. . |
| 5,219,400 | 6/1993 | Jacot et al. . |
| 5,243,983 | 9/1993 | Tarr et al. .............................. 128/633 |
| 5,279,296 | 1/1994 | Thurston et al. . |
| 5,284,149 | 2/1994 | Dhadwai et al. . |
| 5,340,991 | 8/1994 | Fransen et al. . |
| 5,348,018 | 9/1994 | Alfano et al. . |

OTHER PUBLICATIONS

S. Lerman, et al., "Ultraviolet–Visible Slit Lamp Densitography of the Human Eye," *Exp. Eye Research*, 1981, vol. 33, pp. 587–596.

W. Lohmann, et al., "Device for Measuring Native Fluorescence of Lenses," *Journal of Biochemical and Biophysical Methods*, 1988, vol. 17, pp. 155–158.

W. Lohmann, et al., "Distribution Pattern of Native Fluorophores in Cataractous Lenses," Exp. Eye Research, 1990, vol. 50, pp. 227–230.

M. Mosier, et al., "Autofluorescence of the Crystalline Lens in Diabetes," *Arch. Ophthalmology*, Sep. 1986, vol. 104, pp. 1340–1343.

J. van Best, et al., "In vivo Assessment of Lens Transmission for Blue–Green Light by Autofluorescence Measurement," Ophthalmic Research, 1985, vol. 17, pp. 90–95.

J. van Best, et al., "Autofluorescence and Light Scatter in the Human Lens as Measured by a Fluorophotometer," *Exp. Eye Research*, 1989, vol. 49, pp. 511–513.

N. Yu, "Clinical Monitor of Diabetic Lenses by Fluorescence/Raman," Grant No. EY07006–01, May 1986.

N. Yu, "Clinical Monitor of Diabetic Lenses by Fluorescence," Continuation grant No. EY07006–02, Jan. 1988.

N. Yu, "Clinical Monitor of Diabetic Lenses by Fluorescence," Progress report summary—grant No. EY07006–04, Jan. 1990.

N. Yu, et al., "Progress Report," Apr. 1991.

APPARATUS AND METHODS FOR MEASURING CHARACTERISTICS OF BIOLOGICAL TISSUES AND SIMILAR MATERIALS

This application is a continuation-in-part of application Ser. No. 07/731,533 (now U.S. Pat. No. 5,203,328), filed Jul. 17, 1991, entitled "Apparatus and Methods for Quantitatively Measuring Molecular Changes in the Ocular Lens," now U.S. Pat. No. 5,203,328 which application is incorporated herein in its entirety by this reference.

This invention relates to the measurement of the characteristics of biological tissues and similar materials and more specifically to apparatus and methods for quantitatively measuring spectral characteristics of human tissue for the purpose of medical evaluation.

BACKGROUND OF THE INVENTION

Existing methods of spectral examination of biological tissues and other turbid media are often less than desirable. These methods fail to properly normalize for variations in the density, scattering, reflectivity, absorbance and transmittance of such tissues and as a result, have wide variations in the results obtained. Typically, spectral transmittance, fluorescence (normal and time resolved) and Raman spectroscopy are used to evaluate biological tissues and other materials in order to determine the materials present and measure their concentrations. Each of these methods are affected by the scattering, reflecting, absorbing and transmitting properties of the media since the amount of light reaching the tissue is a function of these parameters and in the case of fluorescence and Raman emissions, reabsorption of emission spectra.

In our pending patent application Ser. No. 07/731,533, we discussed the use of new normalization techniques for the detection of cataracts and diabetes. In addition, we are aware of a patent by Schiller, German Patent #261957A1 and R. R. Alfano, U.S. Pat. No. 4,930,516 (which patents are incorporated herein in their entireties by this reference), which refer to the use of the ratio between two fluorescence peaks in fluorescence spectroscopy as normalization techniques. However, since both the target spectra and the reference spectra are affected by scattering and absorption, these techniques are not wholly satisfactory.

SUMMARY OF THE INVENTION

The present invention provides apparatus and methods for characterizing biological tissues and other turbid media with normalization that serves to compensate for the effects of scattering, reflectance, and absorption. Utilizing a beam of electromagnetic or other radiation directed into the tissue or other media to be examined, the pump beam, (preferably a beam of optical radiation at a wavelength between 400 nanometers and 20,000 nanometers) and a suitable detector directed toward the volume of the tissue or other material to be characterized, the receiver, a measurement is made of the amount of the pump beam returned to the receiver by effects such as scattering, reflection, or other similar effects. A measurement is also made of the physical parameter of interest, which could be transmission or emission. Emission, such as Raman emission or fluorescence emission is typically at a wavelength offset by the pump beam by an amount and intensity dependent on the particular chemical properties of the material. Other methods, such as time-resolved spectroscopy could also be used. Normalization of the material under examination is achieved by using the intensity or other characteristics of the unshifted scattered, reflected, or otherwise modified beam. In the simplest of systems, the normalization is accomplished by using the ratio of the emission intensity to the scattered or reflected intensity.

The process of normalization can be improved further by the use of a confocal arrangement with a wide cone between the receiver and the pump beam. If the pump beam is directed into the tissue via a focusing arrangement with a wide focusing cone and a small focal volume and the receiver field of regard is limited to the small focal volume, the normalization is further improved. If the media to be characterized is a human eye, the receiver is preferably slightly off axis from the axis of the pump beam so as to eliminate specular reflections from the received signal and improve the effects of the normalization.

It is therefore an object of the present invention to provide apparatus and methods for normalization of various spectroscopic techniques for accurate use in biological tissues and other turbid media.

It is another object of the present invention to provide apparatus and methods suitable for compensating for scattering and density differences encountered when making measurements in turbid media.

It is yet another object of the present invention to provide apparatus and methods for eliminating the effects of specular reflections from media with highly reflective boundary layers, such as the human eye.

It is a further object of the present invention to provide apparatus and methods for determining characteristics of tissue, including ones related to the level of glycation in the tissue or in other tissues such as the blood.

It is a further object of the present invention to provide apparatus and methods for determining characteristics of tissue, including ones related to the level of glycation in the tissue or in other tissues such as the blood.

Other objects, features and advantages of the present invention will become apparent with reference to the remainder of the written portion and drawings of this application.

BRIEF DESCRIPTION OF THE INVENTION

DETAILED DESCRIPTION

Figure 1:
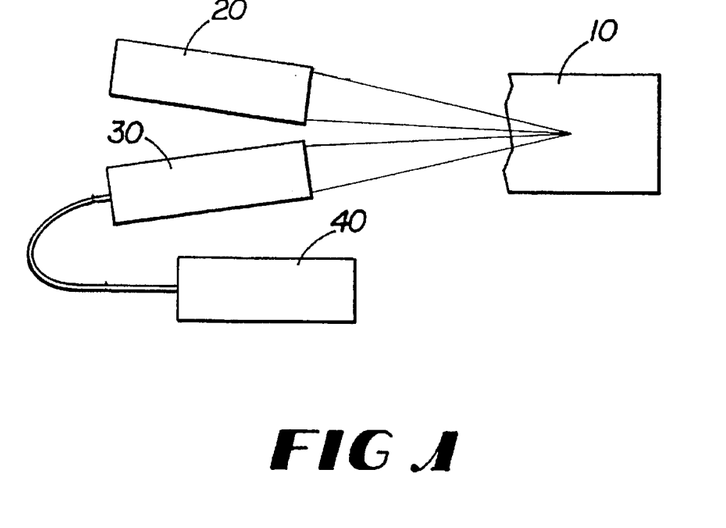
FIG. 1 is a schematic representation of an apparatus of the present invention.

FIG. 1 illustrates a schematic layout of the present invention. The FIG. 1 shows a illuminating source 20, which is directing electromagnetic radiation into the media to be examined 10. A collecting, separating and detecting means 30, is shown oriented toward the media to be examined 10. A processing means is shown for determining the mathematical relationship between the separated radiation 40.

Further information concerning the subject matter of the present invention can be obtained from the following article authored by two of the named inventors (J. Eppstein & S. Bursell, "Non-invasive detection of diabetes mellitus"):

Recent advances in fluorescence spectroscopy of the lens reveal the potential of a non-invasive device and methodology to sensitively measure changes in the lens of the eye associated with diabetes mellitus. The system relies on the detection of the spectrum of fluorescence emitted from a selected volume (approximately $\frac{1}{10}$ mm$^3$) of the lens of living human subjects using low power excitation illumination from monochromatic light sources. The sensitivity of this technique is based on the measurement of the fluorescence intensity in a selected region of the fluorescence spectrum and normalization of this fluorescence with respect to attenuation (scattering and absorption) of the incident excitation light. The amplitude of the unshifted Rayleigh line, measured as part of the fluorescence spectrum, is used as a measure of the attenuation of the excitation light in the lens. Using this methodology we have demonstrated that the normalized lens fluorescence provides a more sensitive discrimination between diabetic and non-diabetic lenses than more conventional measurements of fluorescence intensity from the lens. The existing instrumentation will be described as well as the proposed design for a commercial version of the instrument expected to be ready for FDA trials by late 1992. The results from clinical measurements are used to describe a relationship between normalized lens fluorescence and hemoglobin A1c levels in diabetic patients.

1. INTRODUCTION

Over the last two decades, a good deal of research has been done to characterize the fluorescent response of the human lens. Researchers have searched to uncover correlations between detected shifts in the lens' optical properties and the physiological condition of the subject under test. Previous research has established some correlation between the fluorescent response of the lens and the subjects age and the presence of diabetes. The work described in this paper continues in this direction, with the focus being to refine the apparatus and method such that a non-invasive test for the detection of diabetes mellitus becomes possible.

In the case of Type I, or juvenile diabetes, early detection can significantly benefit the patient. Some research has indicated that if detected early enough, the onset of full blown Type I diabetes maybe delayed for several years with new developments in immunosuppressive drug therapy. Type I diabetes is essentially an auto-immune disease in which the immune system attacks the insulin producing islet cells in the pancreas. Because of this, early detection of Type I diabetes is possible in some patients, through the use of a complex test for antibodies to the pancreatic islet cells. (Islet Cell Antibody test or ICA). Unfortunately, standardization of the ICA test is not yet sufficient for most diabetologists to prescribe it routinely. However, when the ICA test has been applied properly, a model developed by Jackson et. al. has shown that it can detect a prediabetic condition of Type I diabetes several years before overt clinical symptoms of the disease are present. One of the most provocative results of the work described here, is its' apparent ability to detect this prediabetic condition when no other symptoms are present.

Another blood test which is routinely prescribed for diagnosed diabetic patients is a measure of the serum hemoglobin A1c levels. Measuring the glycosylation of the patients hemoglobin, this test gives the clinician a quantitative measure of how well the patient has controlled their blood glucose levels over the last 6 to 10 weeks. The A1c test is routinely prescribed every one to three months for most type I diabetic patients and at least twice a year for most type II diabetic patients. The A1c test is generally accepted as the best indicator of the efficaciousness of a prescribed treatment regimen for a diabetic. Upon initial diagnosis, the A1c test is used even more frequently to fine tune a treatment program. A definite correlation has been observed between the fluorescence ratio measurements made with the system and a diabetic subject's A1c levels. A model for estimating the A1c level as a function of age and Fluorescence/Rayleigh Ratio has been developed.

Figure 1A:
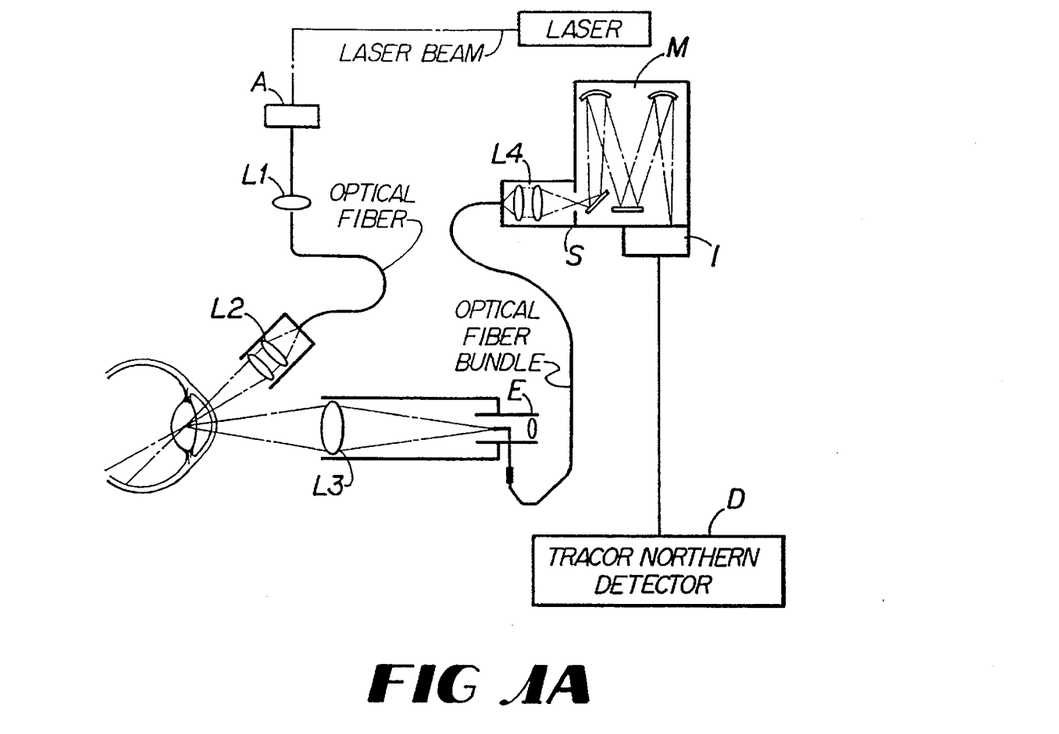
FIG. 1A is a schematic representation of a prototype system in accordance with the present invention.

The prototype system utilizes a low power laser to excite a fluorescent response in a small volume of the ocular lens tissue. A schematic representation of this system is shown in FIG. 1A. The system allows the illumination source to be selected from lasers emitting at 406.7 nm, 441.6 nm, 488 nm, or 514.5 nm. An optical collection system, aligned confocally with the illumination system, is used to gather the entire spectrum of the fluorescence response as well as the backscattered Rayleigh radiation from the lens. The optical design of the system is such that specular reflections of the incident light from the cornea and lens capsule are excluded from the collection system. The collection optics also provide the operator with an eyepiece through which the operator views the area in the lens which is currently being targeted. The collected light, both emitted fluorescence and backscattered excitation light, is delivered to a spectrometer which focuses the spectrum onto an intensified diode array detector. The intensity spectrum of the emitted fluorescence is thus recorded together with the unshifted Raleigh component for subsequent processing.

The emitted fluorescence in a defined spectral region is normalized using the amplitude of the unshifted Rayleigh components. This fluorescence ratio provides a good discrimination between lenses of diabetic and non-diabetic subjects.

2. METHODS 2.1 Instrumentation

A unique optical system has been devised which allows the user to selectively target small volumes within the lens for excitation with a light source. The laser light used in this system is directed through a variable optical attenuator (A) and then focused onto the end of a 140 micrometer fiber optic. The fiber optic routes the laser light to the delivery optics (L2). Using a modified slit lamp base to support both the delivery optics (L2) and collection optics (L3), a confocally aligned collection system allows this same small volume to be examined. An eyepiece (E) allows the operator to view directly the area being targeted. A fiber optic bundle positioned in the collection optics carries the collected light to a spectrometer (S) which is in turn connected to a computer controlled data acquisition system.

Both the backscattered Rayleigh radiation and the excited fluorescent radiation being emitted from the targeted volume within the lens are collected and directed into the spectrometer with its enhanced diode detector array (D). The relatively large focal cone of both the delivery and the collection optics, and the small spot size illuminated and imaged, allows the operator to easily distinguish the boundaries at both the anterior and the posterior of the lens merely by observing the visual change in the image as seen through the eyepiece.

A position sensor attached to the modified slit lamp allows the automatic registration of the position in the lens from which a given spectrum was recorded. The operator, under direct visualization, marks both the anterior and posterior lens capsule positions along the visual axis, within the lens, and the position from which each spectrum was taken is recorded.

The instrument can be used on either dilated or undilated eyes. When used on undilated subjects, closer attention must be made to the positioning of the instrument to exclude the possibility of collecting a specularly reflected component of the source if it were to hit the iris. To verify the useability of the instrument on undilated subjects, several subjects have been measured twice, once dilated and once undilated, and the results have been shown to be the same. This is important for any non-invasive testing device.

Figure 2:
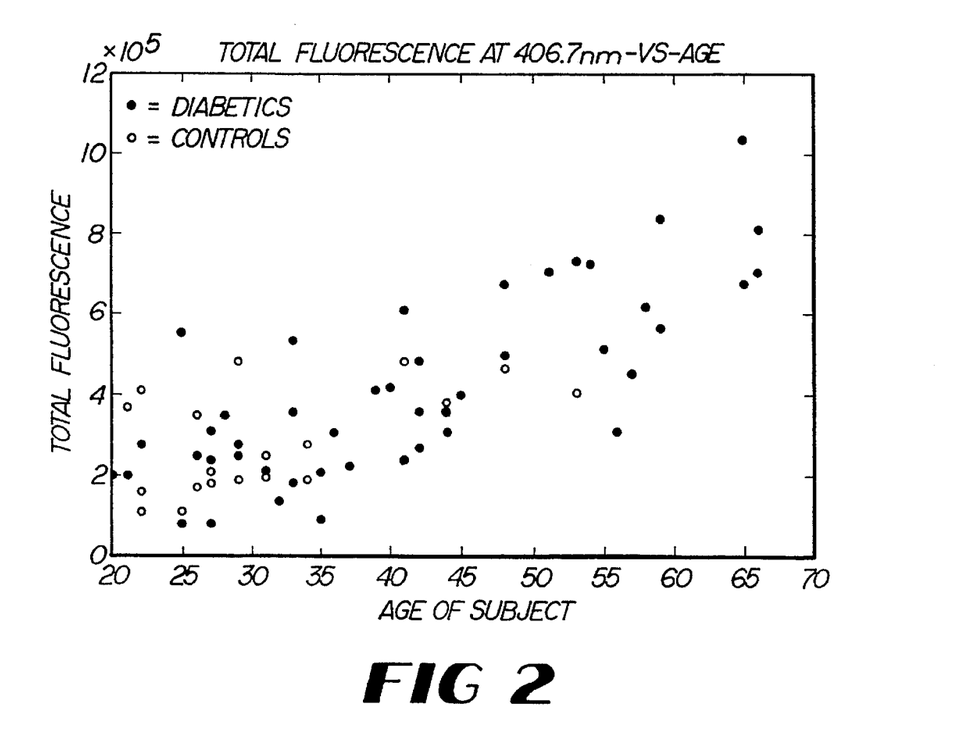
FIG. 2 is a graphical representation of an example of the fluorescent signal intensity obtained using the apparatus of FIG. 1.
Figure 2A:
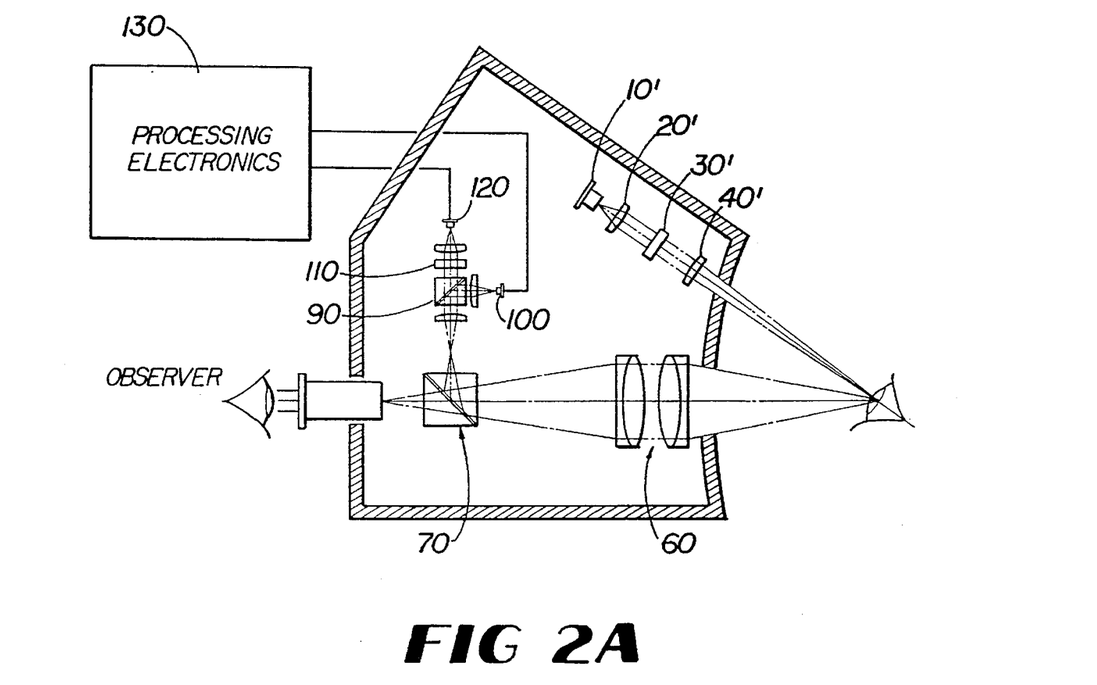
FIG. 2A is a schmetic representation of an alternative prototype system in accordance with the present invention.

The prototype instrument can easily be modified to provide a portable instrument with commercial potential. Having determined which wavelength to use for the source and which portion of the recorded spectrum to examine to measure the fluorescent response, it is possible to design a much simpler, dedicated system, capable of making the same measurement. This is illustrated in FIG. 2A. By using custom optics to both deliver (20' and 40') and collect (60) the light, one achieves a direct optical path through optical filters (110) and dichroic beam splitters (70 and 90) to discrete photo-detectors (100 and 120). In comparison to the prototype's fiber coupled spectrometer and diode array, optical efficiency may be increased by several orders of magnitude.

With this increase in detection efficiency, the source intensity may be correspondingly lowered, thereby relaxing the requirement that a laser be used for the source. Design analysis has shown that a low power, short arc lamp, with appropriate optics and an optical filter can provide enough optical power. Other sources being investigated include laser diodes (10') coupled to frequency doubling device (30'), blue LEDs and filtered, special purpose incandescent lamps. To exclude specular reflections from the detectors, polarization filters are proposed for both the transmit and receive optics.

The electronics associated with the detection and processing (130) consist of the two analog preamps used with the detectors, and a single chip microcontroller equipped with onboard analog to digital (A/D) conversion. Embedded firmware would direct the operator through a measurement event and then either display the processed measurement information on the systems own digital display, or log this data to a computer via a serial interface.

2.2 Patient Measurement Protocol

Prior to patient measurements the level of the incident excitation illumination is set using fluorescence measurements from a fluorescent glass standard. The incident illumination is adjusted using a variable attenuator in the path of the laser beam. The source intensity is set to provide a fixed level of fluorescence intensity which corresponds to an illumination power level of less than 500 microwatts of continuous power.

The subject is then seated at the slit lamp and asked to position their head in the head rest provided and look at the fixation target. The operator, while directly viewing the lens through the eyepiece, brings the focal plane of the viewing and illumination optics into the central region of the lens of the eye by adjusting the position of the slit lamp. The fixation target is then adjusted to ensure that specular reflections from the cornea and lens capsule are excluded from the collection optics. The anterior and posterior capsule boundaries are marked using the position sensor attached to the slit lamp as it is scanned along the visual axis of the lens. Having located the positions of the front and rear of the lens the operator then scans along the visual axis of the lens selecting points from which fluorescence spectra are recorded. The positions at which each spectra were obtained are also recorded. Typically, 10 spectra are recorded along this visual axis. The exposure time required for each spectrum is 2 seconds. This time was chosen as a compromise between excitation light exposure, signal-to-noise ratio of the recorded spectra and the time during which a subject could comfortably keep their eye open without blinking.

2.3 Data Analysis

The total fluorescence emitted from a region in the lens, at a given excitation intensity, can be affected by absorption and scattering attenuation, not only of the incident excitation but also of the emitted fluorescence. Increases in scattering will decrease the available excitation energy delivered to the sample region of the lens and decrease the emitted fluorescence intensity collected by the collection optics. Increased absorption in front of the sample region will also decrease the delivered excitation energy and the emitted fluorescence intensity. Thus when comparing two lenses, for example, both having the same concentration of lens fluorophore but with one lens being more highly scattering than the other, the lens exhibiting the higher scattering will show an apparent decrease in fluorescence intensity compared to the less scattering lens.

The attenuation effects of lens scattering and lens absorption can be corrected for by normalizing the emitted fluorescence with respect to the actual intensity of incident excitation illumination delivered to the sample region. Thus, forming the ratio between the fluorescence intensity and the Rayleigh intensity provides a normalization of the fluorescence intensity. This fluorescence ratio thus provides a basis for quantitative comparisons between different lenses.

Further specificity in analyzing lens fluorescence is realized by analyzing specific spectral regions of the recorded spectra. It has been demonstrated that the aging lens contains a number of different fluorescing proteins exhibiting fluorescence at longer and longer excitation wavelengths. For example, in older lenses and brunescent cataracts there exists a significant red fluorescence. By restricting the spectral region from which fluorescence measurements are made, at a given excitation wavelength, it is possible to isolate the characteristics of a relatively distinct species of lens protein fluorophores.

The effectiveness of our lens fluorescence normalization procedure was tested by scanning through the glass fluorescence standard at the different excitation wavelengths used. The fluorescence ratio remained constant (±5%) through the glass despite significant absorption as noted by a 3-fold reduction in the intensity of the Rayleigh line and a concomitant reduction in the measured fluorescence intensity.

At each excitation wavelength used 406.7 nm, 441.6 nm, 488 nm, and 514.5 nm, the measured fluorescence spectra from the lens exhibited intensity maxima in the 490 nm, 520 nm, 540 nm, and 550 nm wavelength regions respectively. Analysis involved calculating the fluorescence ratio using average fluorescence in a 10 nm spectral region centered about the wavelength at which the fluorescence intensity maximum occurred. The fluorescence ratio is defined as the ratio of this fluorescence to the intensity of the backscattered Rayleigh component. The data presented in this paper are the average of the fluorescence ratios obtained from the lens nucleus.

3. RESULTS

The data presented here were obtained using excitation wavelengths of 406.7 nm and 441.6 nm. The capability of measuring fluorescence spectra at the longer excitation wavelengths has only recently been incorporated into the instrumentation and clinical measurements are currently in progress.

Figure 3:
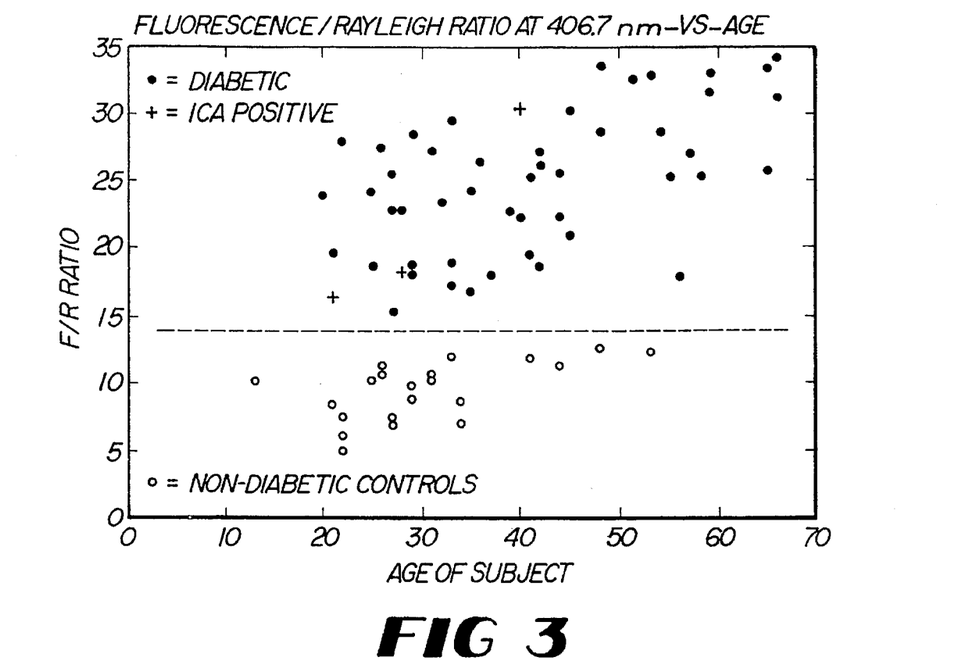
FIG. 3 is a graphical representation of an example of the ratio of the fluorescent to backscattered signal intensities as measured in the lens of a human eye (turbid media) using the apparatus of FIG. 1.
Figure 3A:
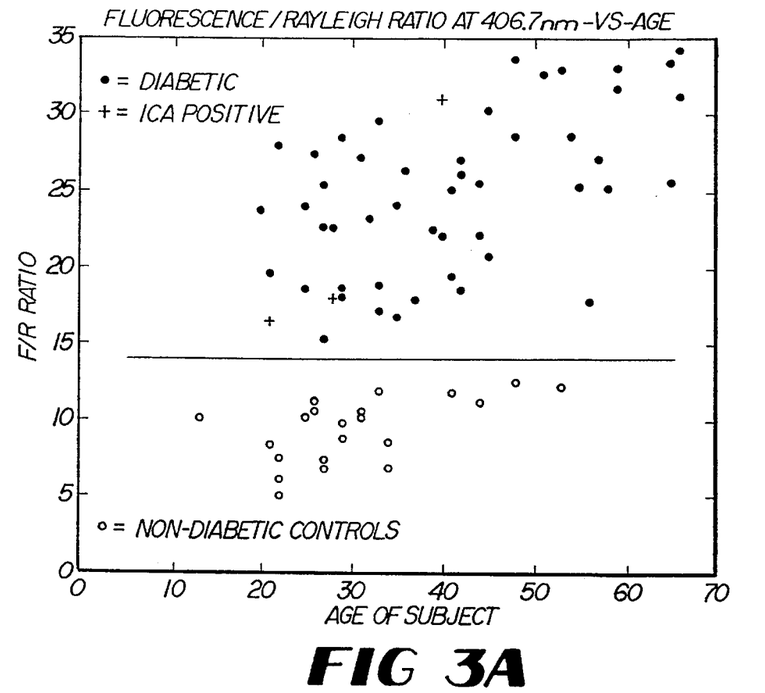
FIGS. 3A and 4A are graphical representations of data obtained using an excitation wavelength of 406.7 nm.
Figure 4:
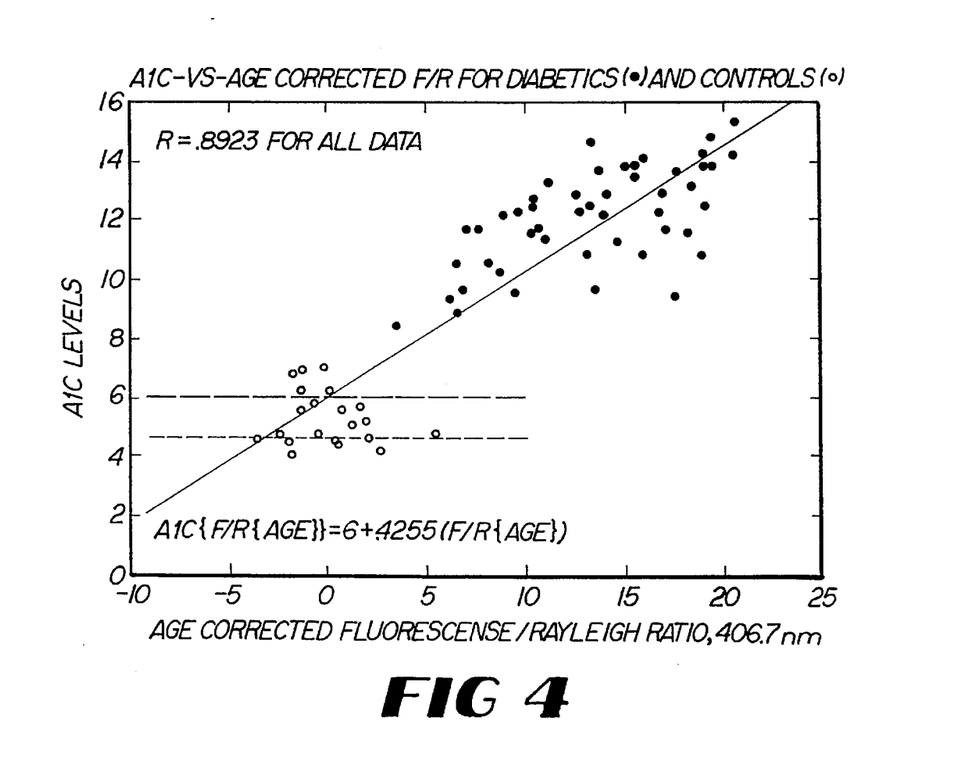
FIG. 4 is a graphical representation of the mathematical relationship between fluorescence and Hemoglobin A1c.
Figure 4A:
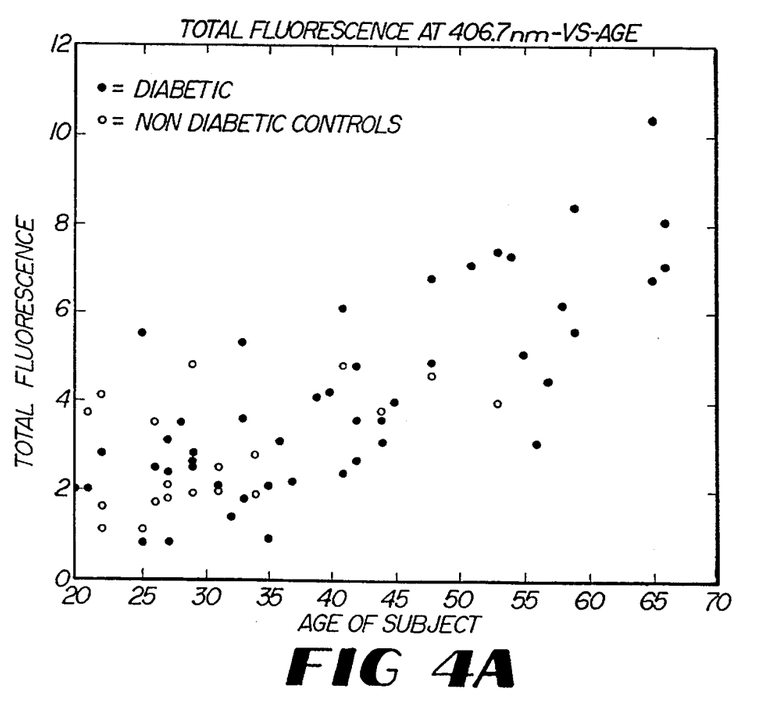

The data obtained using the 406.7 nm excitation wavelength is illustrated in FIGS. 3A and 4A. FIG. 3A illustrates the fluorescence ratio data, using the fluorescence intensity emitted in the 490 nm region of the spectrum detected versus subject age for both diabetic and non-diabetic subjects. As can be noted there is a marked separation between the diabetic and non-diabetic subject's fluorescence ratios. In contrast, FIG. 4A illustrates the same data except that the total emitted fluorescence was calculated by integration of the recorded spectrum and the fluorescence intensity was not normalized with respect to the delivered excitation energy. In this case, for the same subjects as in FIG. 3A, the distinction between diabetic and non-diabetic lenses is considerably less remarkable.

Figure 5:
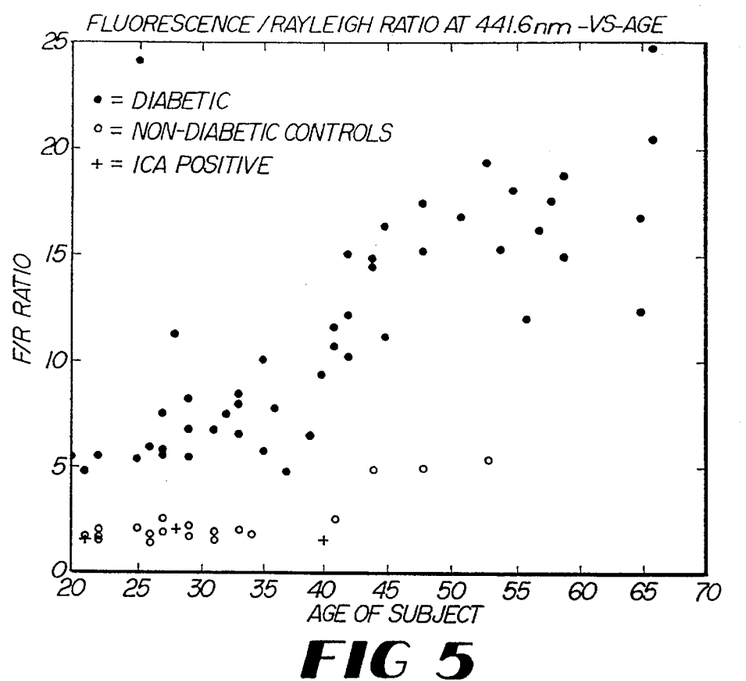
FIG. 5A is a graphical representation of data on fluorescence ratios obtained using an excitation wavelength of 441.6 nm.

FIG. 5 shows the data on fluorescence ratios obtained using the 441.6 nm excitation wavelength. In this case the increase in lens fluorescence ratio with age is more marked, however, the discrimination between diabetic and non-diabetic lenses is less pronounced in subjects less than 40 years old compared to the results obtained using 406.7 nm excitation wavelength.

Comparing FIGS. 3A and 5A also illustrates how the 406.7 nm excitation wavelength (FIG. 3A) produced fluorescence ratios of the three (3) subjects who tested ICA positive, but otherwise have no diabetic symptoms, which groups them with the diabetic subjects. Conversely, the 441.6 nm excitation wavelength (FIG. 5) produced fluorescence ratios which group these three (3) subjects within the non-diabetic control population.

3.1 Age dependence of the fluorescence ratio at 406.7 nm

Studies of the human lens have shown a definite age dependant component of the lens' transmission at all wavelengths from 300 nm to 800 nm. (Lerman, Hockman 1981; Lerman, Hockman, Ohrloff, 1984). At the specific wavelength of 406.7 nm, it has been shown that the lens' transmittance drops from almost 100% in a newborn to about 25% by the age of 25. While the exact relation between absorption at 406.7 nm and the fluorescence response to that wavelength is not known, some trends can be inferred from our knowledge of transmittance. For a newborn, no fluorescence response would be expected, as the lens is almost 100% transmissive at 406.7 nm. The rate of increase in the fluorescence versus age would be expected to increase most rapidly over the first 20 years, by which time the lens is now absorbing 70% to 80% of light at 406.7 nm. This trend would then be expected to increase more gradually for the remaining 60 years, proportional to the continued gradual increase in absorption.

A quadratic model to describe F/R{AGE}, at 406.7 nm, has been derived from the control population data and the assumptions made by inference from the lens transmittance data. Also, the assumptions that additional limiting factors will come into play as one ages, and that the age dependency can be decoupled from other factors affecting the F/R have been incorporated into the derivation of the model presented here.

$$F/R(AGE)=0.38(AGE)-0.0023(AGE)^2$$

Figure 6:
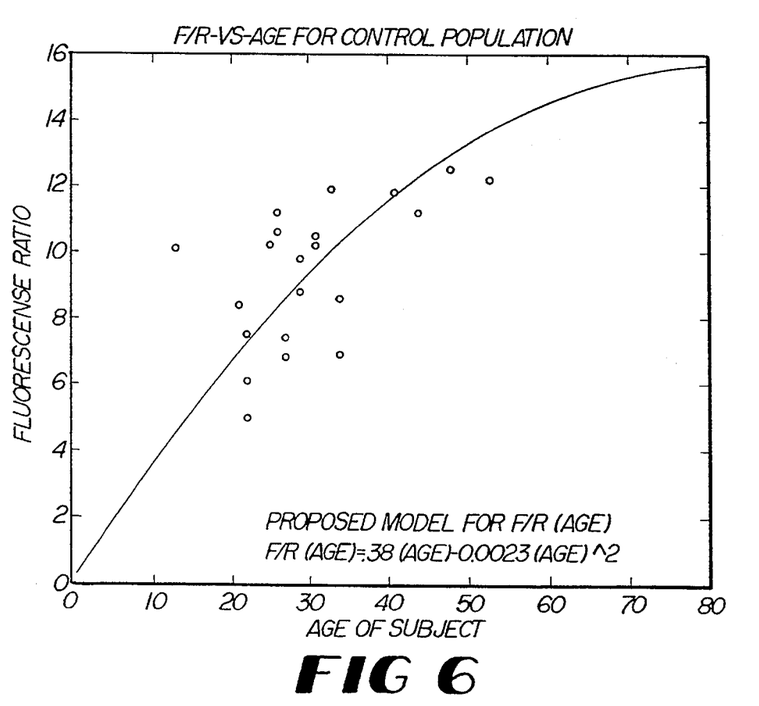
FIG. 6 is a graphical representation of data and a proposed mathematical model of age dependence of the fluroescence ratio.

A graph of the raw data and the proposed model is presented in FIG. 6.

Figure 7:
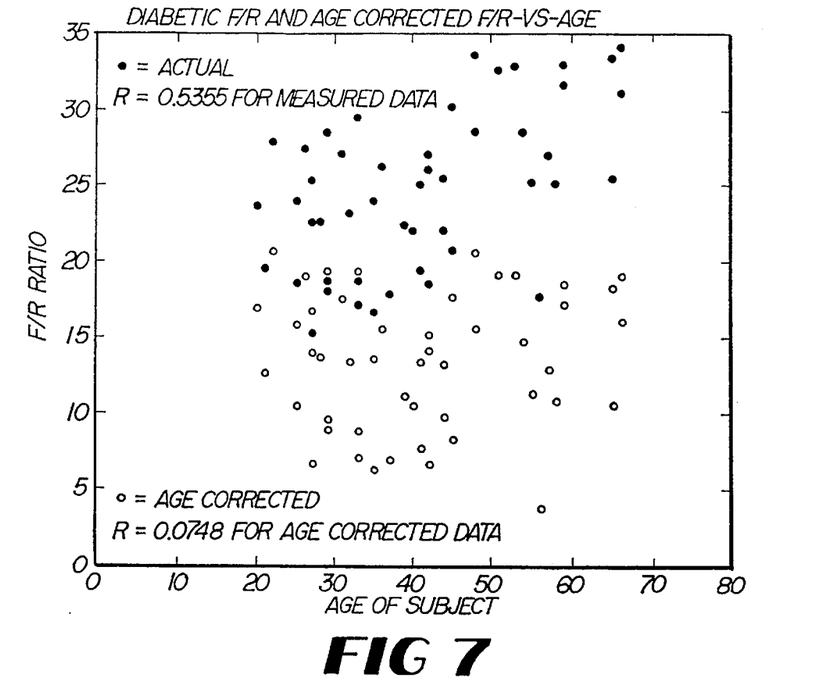
FIG. 7 is a graphical representation of the model proposed in connection with FIG. 6 as compared with data measured from a diabetic population.

This relationship was obtained by setting boundary values on the two end points of F/R(0)=0 and F/R(80)=16, and then applying a second order regression to fit the resulting curve to the control data in a least squares sense. This model meets the criteria of starting at zero, rising most rapidly in the first 20 years, and then approaching a final limiting value more gradually over the next 60 years. By deriving this model on the data taken from only the control population and the assumptions stated, a rough test of its' validity can be made by applying it to those data points measured from the diabetic population used in this study and evaluating the shift in the correlation coefficient. This is shown in FIG. 7. Before the model was applied, the correlation coefficient between the F/R and the subjects age was shown to be (0.5355), after the hypothesized age dependency was subtracted from the data, the resulting data set showed a correlation coefficient between the F/R{AGE_CORRECTED} and the subjects age to be (0.0748). This reduction of the correlation coefficient confirms, to some degree, the correctness of the model. An additional validation of this model and the assumption of independence is provided when the relationship between the A1c levels and the F/R is examined in the following section.

3.2 Correlation of hemoglobin A1c and the fluorescence ratio at 406.7 nm

An apparent correlation between the A1c levels and a subjects F/R values could be discerned for the diabetic population for whom the A1c data was available.

To develop a model for estimating the underlying relationship between A1c and F/R the following assumptions were made:

a.) The age dependent component of the F/R is completely disjointed from the A1c dependent component. This assumption is confirmed to some degree by the observed increase in the correlation coefficient (increased to 0.6385 for the age corrected data from 0.465 for the measured data) relating both the age corrected and the measured F/R to the A1c levels of the diabetic population. This increase in the correlation coefficient also provides further validation of the model derived from F/R{age}, i.e., if the model was inherently incorrect, applying it would redistribute the data such that any other correlations would be made more difficult to uncover.

b.) All of the control population have A1c levels failing within a 'normal' range of between 3 and 7. (Diabetologists typically assume that the upper limit for A1c in a non-diabetic is 6.2 and a practical lower limit is around 3.5)

c.) That the shifts in A1c levels are proportional to the shifts in F/R.

Figure 8:
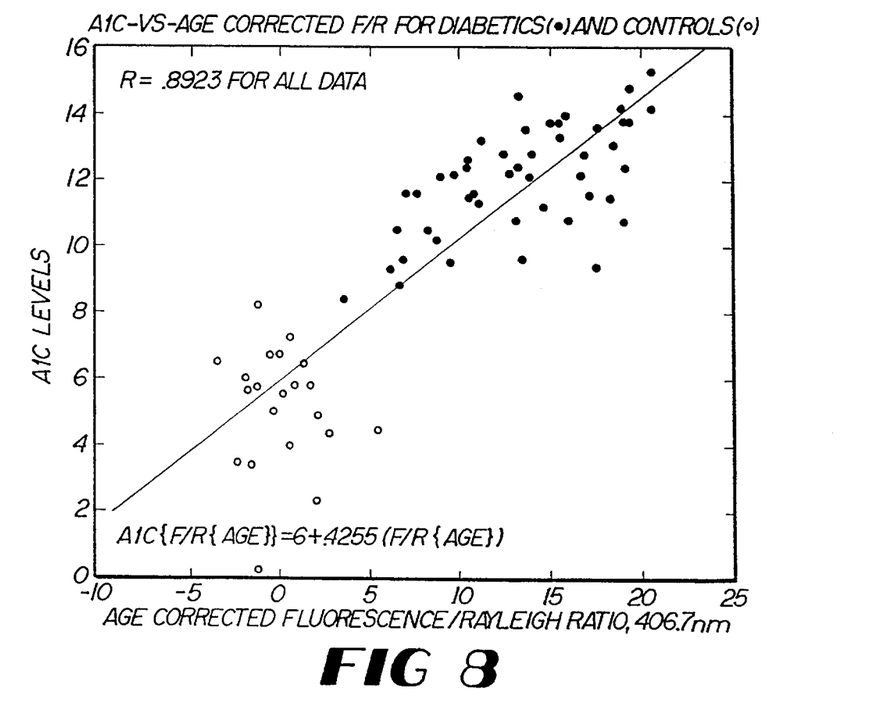
FIG. 8 is a graphical representation of A1c levels versus age corrected fluorescence ratios of both the diabetic and control populations.

Applying assumption (b) a random number generator was used to arbitrarily assign A1c values to the control population with a normal distribution centered at 5 and having a variance of 2. FIG. 8 illustrates this data. The horizontal axis shows the Age corrected F/Rs of both the diabetic and the control populations while the vertical axis shows the A1c levels for each subject. The correlation coefficient for the data shown in FIG. 8 was found to be (0.89). A linear regression was then applied to fit a straight line approximation for the relationship between the age corrected F/R and the A1c level to this data. The resulting relationship is:

$$A1c\{F/R\{AGE\_CORRECTED\}\}=6 \div 0.4255(F/R\{AGE\_CORRECTED\}$$

Whereas F/R{AGE_CORRECTED}=F/R–F/R(AGE)=F/R–[0.38(AGE)–0.0023(AGE)$^2$] we have $$A1c\{F/R,AGE\}=6+(0.4255)(F/R)-(0.162)(AGE)+(0.00098)(AGE)^2$$

4. DISCUSSION AND CONCLUSION

Results to date demonstrate that the specificity of lens fluorescence normalization using a selected spectral bandwidth from the emitted lens fluorescence spectrum provides a sensitive non-invasive technique for evaluating changes in the lens fluorescence associated with diabetes.

The age dependence of increasing fluorescence ratio at 406.7 nm excitation wavelength appears to level off after approximately age 40. In contrast the age dependence of fluorescence ratios at 441.6 nm excitation wavelength appear to be relatively level in subjects under age 40 with an accelerated increase with age in older subjects. This phenomenon may be related to the internal conversion of shorter wavelength excitation lens fluorophores to longer wavelength excitation species in the aging lens. Thus the accumulation with age of the species excited primarily at 406.7 nm is offset by a decrease in their concentration as they are converted into longer wavelength excitation species, as evidenced in the increasing concentration of the 441.6 nm excitation species with age.

While variances occur in the absolute values of the detected fluorescence and backscattered Rayleigh components along the radial axis of the lens, when the ratio is formed the normalization which occurs nulls these differences. By design, the delivery and collection optics are focused on the same point in space. The intersection of the focal waists define a volume of approximately 0.12 mm$^3$. Also, both the instrumentation and the methodology has been designed to eliminate specular reflections from being collected. Thus the Rayleigh component collected can be used as a measure of the total optical energy delivered to the sampled volume. This feature removes the effect of the variances of absolute energies caused by individual differences in the cornea, the aqueous or the lens itself. At these power levels, the fluorescent response is proportional to the amount of stimulus available. Therefore, the ratio of the collected fluorescent and Rayleigh components provides a repeatable, normalized, and dimensionless measurement of the lens' optical properties. Furthermore this type of Rayleigh normalization appears to be applicable at all excitation wavelengths examined so far. The importance of this technique is shown in FIGS. 3A and 4A wherein the difference between the total fluorescence and the normalized fluorescence can clearly be seen.

The usefulness of the device is apparently closely tied to the specific excitation wavelength used. In particular, the two graphs shown in FIGS. 3A and 5 illustrate the difference in specificity provided by a 406.7 nm source versus a 441.6 nm source, when attempting to distinguish a diabetic from a non-diabetic subject. These data also illustrate the potential of the 406.7 nm excitation wavelength to identify the three (3) subjects who tested ICA positive, but otherwise have no diabetic symptoms, as a diabetic. Conversely, the 441.6 nm excitation wavelength classifies these three (3) subjects well within the non-diabetic control population. While three (3) data points are insufficient to state conclusively the ability to detect this prediabetic condition, the possibility of such a test is extremely exciting. More subjects are currently being measured to establish more precisely the specificity of this system for detecting diabetes. Preliminary results at the longer excitation wavelengths of 488 nm and 514.5 nm look promising.

The foregoing is provided for purposes of illustration, explanation, and description of embodiments of the present invention. Modifications and adaptations to these embodiments will be apparent to those of ordinary skill in the art and may be made without departing from the scope or spirit of the invention.

We claim:

1. An apparatus for determining the normalized characteristics of biological tissue or other medium comprising:
   a. means for illuminating the medium with electromagnetic radiation directed into the medium, thereby causing the medium to react with a first action selected from the group consisting of reflecting, backscattering, transmitting, and emitting responsive radiation and a second action selected from the same group excluding the first action;
   b. means for collecting the responsive radiation;
   c. means, connected to the collecting means, for separating the collected radiation into a plurality of components; and
   d. means, connected to the separating means, for (i) measuring the intensity of each of the separated plurality of components and (ii) determining a mathematical relationship between the separated plurality of components.

2. An apparatus according to claim 1 in which the illuminating means comprises:
   a. a light source selected from the group consisting of lasers, laser diodes, laser diodes coupled to nonlinear frequency doubling devices, light emitting diodes and broadband sources coupled to optical filters;
   b. a lens, optically responsive to the light from the light source, for focusing the light; and
   c. a lens system, optically responsive to the focused light, having a focus, and defining an aperture at its focus of less than approximately 1 cm.

3. An apparatus according to claim 1 in which the illuminating means causes the medium to react by emitting responsive radiation, further comprising means for measuring the time difference between illumination of the medium and emission of the responsive radiation.

4. An apparatus for determining the normalized characteristics of biological tissue or other medium comprising:
   a. means for illuminating the medium with electromagnetic radiation directed into the medium, thereby causing the medium to react by emitting responsive radiation, which emitted responsive radiation is selected from the group consisting of fluorescence emission and Raman emission;

b. means for collecting the responsive radiation;

c. means, connected to the collecting means, for separating the collected radiation into a plurality of components; and d. means, connected to the separating means, for (i) measuring the intensity of each of the separated plurality of components and (ii) determining a mathematical relationship between the separated plurality of components.

5. An apparatus according to claim 4 in which the separating means comprises at least one dichroic beam splitter.

6. An apparatus according to claim 5 in which the measuring and determining means comprises at least one single chip detector and the wavelengths of the separated plurality of components are between approximately 430 to 20,000 nanometers.

7. An apparatus according to claim 6 in which the illuminating means further comprises means for adjusting the illuminating electromagnetic radiation.

8. An apparatus according to claim 4 in which the illuminating means includes means for illuminating the medium with electromagnetic radiation of more than one wavelength.

9. An apparatus for determining the normalized characteristics of biological tissue or other medium comprising:

a. means for illuminating the medium with electromagnetic radiation directed into the medium, thereby causing the medium to react with an action selected from the group consisting of reflecting, backscattering, transmitting, and emitting responsive radiation;

b. means for collecting the responsive radiation;

c. means, connected to the collecting means, for separating the collected radiation into a plurality of components;

d. means, connected to the separating means, for (i) measuring the intensity of each of the separated plurality of components and (ii) determining a mathematical relationship between the separated plurality of components; and e. means, using the measured intensities of the plurality of separated components, for diagnosing the condition of the medium for the purpose of making a medical diagnosis, the diagnosing means comprising means for detecting diabetes.

10. An apparatus for determining the normalized characteristics of biological tissue or other medium having a level of glycation comprising:

a. means for illuminating the medium with electromagnetic radiation directed into the medium, thereby causing the medium to react with an action selected from the group consisting of reflecting, backscattering, transmitting, and emitting responsive radiation, which illuminating means includes means for illuminating the medium with electromagnetic radiation of more than one wavelength;

b. means for collecting the responsive radiation;

c. means, connected to the collecting means, for separating the collected radiation into a plurality of components;

d. means, connected to the separating means, for (i) measuring the intensity of each of the separated plurality of components and (ii) determining a mathematical relationship between the separated plurality of components; and e. means, using the responsive radiation, for determining the level of glycation.

11. An apparatus according to claim 10 in which the medium comprises ocular tissue and the glycation level determining means comprises means for relating the level of glycation in the ocular tissue to the amount of hemoglobin in the blood affected by the presence of glucose.

12. A method for measuring the characteristics of biological tissue or other medium that, when illuminated, is capable of reacting by emitting radiation and with an action selected from the group consisting of reflecting, backscattering, and transmitting radiation including Raman and Fluorescent components of determinable intensities and emission lifetimes, comprising the steps of:

a. illuminating the medium with electromagnetic radiation, thereby causing the medium to emit radiation and react with an action selected from the group consisting of reflecting, backscattering, and transmitting responsive radiation;

b. separating the emitted radiation into its Fluorescent and Raman components;

c. measuring at least two values, including at least one of the intensity and emission lifetime of at least one of the separated components; and d. forming a mathematical relationship between at least two of the measured values.

13. A method according to claim 12 in which the illuminating means comprises the steps of:

a. providing a light source selected from the group consisting of lasers, laser diodes coupled to nonlinear frequency doubling devices, light emitting diodes, and broadband sources coupled to optical filters; and b. focusing the light using a lens system having a focus and defining an aperture at its focus less than 1 cm and further comprising the step of comparing the ratio of the detected emitted intensities to the backscattered intensities for the purpose of diagnosing disease.

14. A method according to claim 13 in which the medium has a biochemical composition and the illuminating step comprises illuminating the medium with electromagnetic radiation of more than one wavelength, for diagnosing disease and determining the biochemical composition of the medium.

15. An apparatus for determining the normalized characteristics of biological tissue comprising:

a. means, comprising a pump beam, for illuminating the biological tissue with optical radiation having a wavelength of between approximately 40–20000 nanometers and thereby causing the tissue to react with an action selected from the group consisting of reflecting, backscattering, transmitting, or emitting responsive radiation;

b. means for collecting the responsive radiation;

c. means, connected to the collecting means, for separating the responsive radiation into a plurality of components; and d. means, connected to the separating means, for (i) detecting the intensity of each of the plurality of components and (ii) determining a specified mathematical relationship between the plurality of components.

16. An apparatus according to claim 15 in which the illuminating means further comprises a confocal arrangement having a wide focusing cone and a small focal volume.

17. A method for determining the normalized characteristics of biological tissue or other medium comprising the steps of:

a. illuminating the medium with electromagnetic radiation directed into the medium, thereby causing the medium to react with a first action selected from the group consisting of reflecting, backscattering, transmitting, and emitting responsive radiation and a second action selected from the same group excluding the first action;

b. collecting the responsive radiation;

c. separating the collected radiation into a plurality of components; and d. measuring the intensity of each of the separated plurality of components and determining a mathematical relationship between the separated plurality of components.

18. An apparatus for determining the normalized characteristics of biological tissue or other medium comprising:

a. means for illuminating the medium with electromagnetic radiation directed into the medium, thereby causing the medium to backscatter radiation and react with an action selected from the group consisting of reflecting, transmitting, and emitting responsive radiation;

b. means for collecting the responsive radiation;

c. means, connected to the collecting means, for separating the backscattered radiation from the remainder of the collected radiation to define a plurality of components; and d. means, connected to the separating means, for measuring the intensity of each of the separated plurality of components and determining a mathematical relationship between the separated plurality of components.

19. A method for determining the normalized characteristics of biological tissue or other medium comprising the steps of:

a. illuminating the medium with electromagnetic radiation directed into the medium, thereby causing the medium to backscatter radiation and react with an action selected from the group consisting of reflecting, transmitting, and emitting responsive radiation;

b. collecting the backscattered and responsive radiation;

c. separating the backscattered radiation from the remainder of the collected radiation to define a plurality of components; and d. measuring the intensity of each of the separated plurality of components and determining a mathematical relationship between the separated plurality of components.

* * * * *

UNITED STATES PATENT AND TRADEMARK OFFICE
CERTIFICATE OF CORRECTION

PATENT NO. : 5,582,168
DATED : December 10, 1996
INVENTOR(S) : Mark A. Samuels, Scott W. Patterson, Jonathan A. Eppstein, Nai T. Yu, and Sven-Erik Bursell It is certified that error appears in the above-indentified patent and that said Letters Patent is hereby corrected as shown below:

Delete lines 35-38 of Column 2, which duplicate the prior four lines of that column Signed and Sealed this Sixth Day of May, 1997

*Attest:*

BRUCE LEHMAN

*Attesting Officer*     *Commissioner of Patents and Trademarks*